(12) United States Patent
Solce

(10) Patent No.: US 12,318,319 B2
(45) Date of Patent: Jun. 3, 2025

(54) COMPRESSION BAND FOR MITTENS AND EARS

(71) Applicant: Natasha Solce, Houston, TX (US)

(72) Inventor: Natasha Solce, Houston, TX (US)

( * ) Notice: Subject to any disclaimer, the term of this patent is extended or adjusted under 35 U.S.C. 154(b) by 0 days.

(21) Appl. No.: 17/990,490

(22) Filed: Nov. 18, 2022

(65) Prior Publication Data

US 2023/0079051 A1  Mar. 16, 2023

Related U.S. Application Data

(63) Continuation of application No. 17/275,167, filed as application No. PCT/US2020/035988 on Jun. 3, 2020, now Pat. No. 11,504,256.

(60) Provisional application No. 62/856,628, filed on Jun. 3, 2019.

(51) Int. Cl.
| | |
|---|---|
| *A61F 5/01* | (2006.01) |
| *A42B 1/017* | (2021.01) |
| *A42B 1/0188* | (2021.01) |
| *A42B 1/041* | (2021.01) |
| *A42B 1/22* | (2006.01) |

(52) U.S. Cl.
CPC .............. *A61F 5/01* (2013.01); *A42B 1/017* (2021.01); *A42B 1/0188* (2021.01); *A42B 1/041* (2013.01); *A42B 1/22* (2013.01)

(58) Field of Classification Search
CPC .............. A61F 5/01; A42B 1/041; A42B 1/22
See application file for complete search history.

(56) References Cited

U.S. PATENT DOCUMENTS

| 1,675,864 | A | | 7/1928 | Pekowsky | |
|---|---|---|---|---|---|
| 1,710,188 | A | | 4/1929 | Pekowsky | |
| 2,070,216 | A | | 2/1937 | Rosenberg | |
| 4,011,600 | A | | 3/1977 | Malk | |
| 4,247,097 | A | * | 1/1981 | Schwartz | A63B 21/065 2/160 |
| 4,630,317 | A | | 12/1986 | Brown et al. | |
| 4,656,671 | A | | 4/1987 | Manges | |
| 4,746,313 | A | * | 5/1988 | Bray | A63B 31/04 441/57 |
| 4,768,231 | A | | 9/1988 | Schrack | |
| 4,843,652 | A | * | 7/1989 | Kuwahara | A41D 20/00 2/167 |
| 4,864,662 | A | | 9/1989 | Frank | |
| 5,023,954 | A | | 6/1991 | Lyons | |

(Continued)

OTHER PUBLICATIONS

Written Opinion and International Search Report of PCT/US2020/035988; mailed Sep. 9, 2020.

(Continued)

*Primary Examiner* — Khaled Annis
(74) *Attorney, Agent, or Firm* — Polsinelli PC

(57) ABSTRACT

Mitten and ear compression apparatus including a compression band having a substantially circular shape. The compression band can have a circumferential length and a compression band operably coupled with at least one-half (½) of the circumferential length of the compression band. The compression band can be coupled with less than nineteen-twentieths (19/20) of the circumferential length of the compression band, thereby forming a front portion of the circumferential length not having a compression band coupled therewith.

3 Claims, 5 Drawing Sheets

(56) References Cited

U.S. PATENT DOCUMENTS

| | | | |
|---|---|---|---|
| 5,031,609 A | 6/1991 | Fye | |
| 5,058,606 A | 10/1991 | Malkoff | |
| 5,113,849 A * | 5/1992 | Kuiken | A63B 21/026 601/40 |
| 5,426,789 A | 6/1995 | Macleod | |
| 5,444,874 A * | 8/1995 | Samelian | A41D 19/0013 2/917 |
| 5,548,845 A | 8/1996 | Gallup | |
| 5,774,894 A * | 7/1998 | Yates | A41D 19/0041 2/160 |
| 5,809,569 A * | 9/1998 | Bruno | A41D 19/0034 2/160 |
| 5,820,526 A * | 10/1998 | Hoffman | A63B 21/065 482/55 |
| 5,845,338 A | 12/1998 | Clark | |
| 5,898,943 A * | 5/1999 | Kim | A63B 71/146 2/161.4 |
| 6,227,011 B1 | 5/2001 | Cortinovis | |
| 6,336,224 B1 | 1/2002 | Wang | |
| 6,374,414 B1 * | 4/2002 | Collier | A41D 27/10 2/908 |
| 6,554,787 B1 | 4/2003 | Griffin et al. | |
| 6,571,396 B1 | 6/2003 | Yan | |
| 6,920,644 B1 | 7/2005 | Higgs | |
| 7,761,933 B2 | 7/2010 | Pham | |
| 8,364,220 B2 | 1/2013 | Sandmore | |
| 8,381,731 B2 | 2/2013 | Jundt et al. | |
| 8,621,665 B1 * | 1/2014 | Lowney | A41D 19/01 2/161.1 |
| 8,852,095 B2 | 10/2014 | Schlottau et al. | |
| 9,486,364 B2 | 11/2016 | Servell | |
| 9,654,878 B2 | 5/2017 | Siskin et al. | |
| 9,839,245 B2 | 12/2017 | Bryski et al. | |
| 10,264,836 B2 * | 4/2019 | Duhatschek | A41F 1/06 |
| 10,912,910 B1 | 2/2021 | Yezerski | |
| 2003/0041366 A1 | 3/2003 | Ng | |
| 2003/0131861 A1 | 7/2003 | Prestia | |
| 2004/0010839 A1 | 1/2004 | Cheatum | |
| 2004/0040066 A1 | 3/2004 | Hardenbrook | |
| 2004/0200494 A1 | 10/2004 | Lee | |
| 2005/0137663 A1 | 6/2005 | Lopez et al. | |
| 2006/0179544 A1 | 8/2006 | Knievel | |
| 2007/0061943 A1 * | 3/2007 | Kleinert | A41D 19/01576 2/159 |
| 2007/0079423 A1 | 4/2007 | Flatt | |
| 2007/0167899 A1 | 7/2007 | Strom | |
| 2007/0199151 A1 | 8/2007 | Brown et al. | |
| 2008/0216214 A1 | 9/2008 | Dolby | |
| 2009/0013449 A1 | 1/2009 | Kahn | |
| 2009/0151048 A1 | 6/2009 | Laury | |
| 2009/0255035 A1 | 10/2009 | Little et al. | |
| 2009/0293172 A1 * | 12/2009 | Carota | A41D 19/0034 2/164 |
| 2010/0081904 A1 | 4/2010 | Medina | |
| 2010/0281600 A1 | 11/2010 | Tagg | |
| 2011/0113521 A1 * | 5/2011 | Bradford | A41D 19/01582 2/163 |
| 2011/0197336 A1 * | 8/2011 | Suk | A41D 19/01582 2/161.3 |
| 2012/0179078 A1 | 6/2012 | Koehler | |
| 2012/0296252 A1 | 11/2012 | Cumming et al. | |
| 2013/0219593 A1 | 8/2013 | Snyder | |
| 2013/0227765 A1 * | 9/2013 | Bailey | A41F 1/06 2/311 |
| 2013/0263356 A1 * | 10/2013 | Jones | A63B 71/148 2/163 |
| 2013/0283498 A1 * | 10/2013 | Hewitt | A41D 19/0048 2/163 |
| 2014/0101821 A1 | 4/2014 | Dammann et al. | |
| 2014/0128788 A1 | 5/2014 | Marshall | |
| 2014/0188024 A1 | 7/2014 | Cox | |
| 2014/0207187 A1 * | 7/2014 | Kiraly | A41D 19/0037 606/223 |
| 2014/0221114 A1 * | 8/2014 | Woody | A63B 69/0059 473/213 |
| 2014/0373278 A1 | 12/2014 | Scott et al. | |
| 2015/0082505 A1 * | 3/2015 | Davis | A41D 11/00 2/20 |
| 2015/0335086 A1 | 11/2015 | Murphy et al. | |
| 2016/0354673 A1 * | 12/2016 | Machado | A41D 19/00 |
| 2017/0000651 A1 | 1/2017 | Cumming et al. | |
| 2017/0188644 A1 | 7/2017 | Foresta et al. | |
| 2017/0209328 A1 | 7/2017 | Kajimoto et al. | |
| 2017/0360138 A1 | 12/2017 | Guice | |
| 2019/0045902 A1 | 2/2019 | Baker | |
| 2019/0133231 A1 | 5/2019 | Stark | |
| 2019/0289948 A1 | 9/2019 | Moroy | |
| 2019/0335827 A1 * | 11/2019 | Bitton | A41D 19/0044 |
| 2021/0120900 A1 | 4/2021 | Stirgus | |
| 2021/0204630 A1 | 7/2021 | Baylor et al. | |
| 2021/0259346 A1 | 8/2021 | Hodgdon et al. | |
| 2022/0031001 A1 | 2/2022 | Binns et al. | |
| 2022/0125140 A1 * | 4/2022 | Li | A41D 19/0034 |
| 2022/0240608 A1 * | 8/2022 | Garelick | A41D 19/01 |

OTHER PUBLICATIONS

Oto Band retrived from http://nouvelleinc.com/otoband.aspx; retrived on Jun. 28, 2019.

https://www.amazon.com/Ear-Band-ULTRA-Swimming-Headband/dp/B07C1BQ291; retrived on Jun. 28, 2019.

https://www.sculpturegarments.com/products/popular/female-garments/female-facial-garments/otoplasty-compression-strap/?v=7516fd43adaa; retrived on Jun. 28, 2019.

* cited by examiner

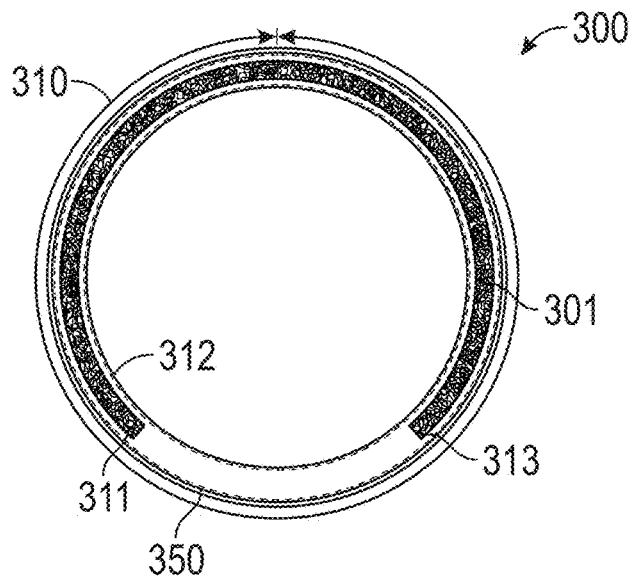

802
Receive an ear compression band having a substantially circular shape and the ear compression band having a circumferential length, the ear compression band having a compression band operably coupled with at least one-half (1/2) of the circumferential length 804
Position the ear compression band on a user's head with the compression band disposed on a rear portion of a user's head, wherein the compression band has longitudinally distal ends with a first distal end is arranged at one user's ear and a second distal end arranged at the user's opposing ear 806
Adjust a fastening system coupled with the ear compression band, thereby reducing and/or increasing the circumferential length of ear band based on the user's head size

FIG. 8

COMPRESSION BAND FOR MITTENS AND EARS

CROSS-REFERENCE TO RELATED APPLICATIONS

This application is a continuation of U.S. patent application Ser. No. 17/275,167, now U.S. Pat. No. 11,504,256, filed Mar. 10, 2021, which is a National Stage entry of PCT/US2020/035988, filed Jun. 3, 2020, which claims the benefit of U.S. Provisional Application No. 62/856,628 filed Jun. 3, 2019, the contents of each of which are incorporated in their entirety herein.

FIELD

The subject matter herein generally relates to an ear compression band and mittens.

BACKGROUND

In regards to the medical issue, many newborns have ears that abnormally stick out and parents have a brief timeframe for a noninvasive solution. Whereas none of the solutions guarantee an outcome, all of them bring undesirable social attention to the deformity. Additionally, hats for infants and toddlers usually have issues like falling off, causing indentions to the head, and a finite option of hat styles.

BRIEF DESCRIPTION OF THE DRAWINGS

Implementations of the present technology will now be described, by way of example only, with reference to the attached figures, wherein:

FIG. 7E is a top sectional view of a mitten fastener system, according to at least one instance of the present disclosure;

FIG. 8 is a flow chart of a method of use for an ear compression band, according to at least one instance of the present disclosure.

DETAILED DESCRIPTION

Figure 1:
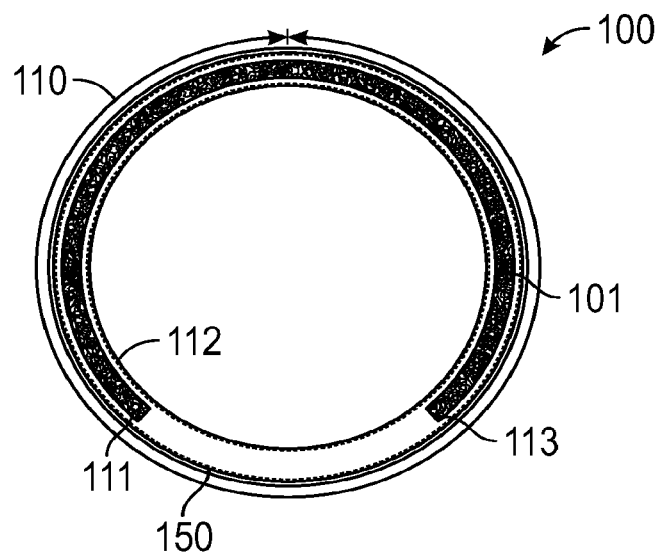
FIG. 1 is an example top sectional view of an ear compression band, according to at least one instance of the present disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising" means "including, but not necessarily limited to"; it specifically indicates open-ended inclusion or membership in a so-described combination, group, series and the like.

The present disclosure is drawn a headband and/or hat for use with newborn babies and/or infants. The headband and/or hat can be configured as described herein to enhance the ability of the headband and/or hat to stay on the head of newborn babies and/or infants. In at least one instance the headband and/or hat can be for use with newborn babies and/or infants having one or more prominent ears, protruding ears, and/or malshaped ears. These conditions can be readily corrected early in a child's life and may or may not require medical intervention. The bulk of the disclosure presented herein focuses on the assistance with treating one or more of the above conditions, but the present disclosure can equally function to retain the headband and/or hat on the head of a user without one of those conditions and/or covering the ears of user undergoing treatment for one of the above conditions. For instance, the headband and/or hat can cover tape or other devices operable to treat one of the above conditions.

A compression headband and/or hat, as disclosed, can be implemented to correct and/or assist in recovery by positioning the ear flat against the child's head in a more natural position, thereby allowing healing of tissue and/or hardening of ear cartridge to occur in the correct position. The present disclosure is described in relation to the relational placement of the three main parts: (1) a compression band, (2) a hat, namely hat rim, and/or (3) a fastener. The present disclosure is generally relates to an ear compression device having a substantially circular headband with a compression band operably coupled with at least a portion thereof. The compression band being disposed circumferentially around at least one-half (½) of the headband. The compression band can be disposed within a slot formed within a portion of the headband. The compression band can also be disposed within a portion of material making up the headband and/or hat. While the compression band is generally illustrated as being continuous, the compression band can be made into two portions. In at least one instance, the compression band can span to cover each ear of the user, but not be directly connected rather being coupled through the headband.

The headband can include a fastening system operable to reduce a circumferential length of the substantially circular headband. The headband can further include a hat portion extending from an upper edge of the headband. The hat portion can be substantially dome-shaped (e.g. frusto-spherical), frusto-conical, and/or other shape-arrangements.

FIG. 1 illustrates the top sectional view of an ear compression band, according to at least one instance of the present disclosure. An ear compression band 100 can have a compression band 101 operable coupled with at least a portion thereof. The ear compression band 100 can be substantially circular, and the compression band 101 can be coupled with at least one-half (½) of a circumferential length 110 of the ear compression band 100. In some instances, the compression band 101 can be arranged and/or coupled with no more than approximately nineteen-twentieths (19/20) of the circumferential length 110 of the ear compression band 100. In some instances, the compression band 101 can be arranged and/or coupled with between approximately seventeen-twentieths (17/20) of the circumferential length 110 of the ear compression band 100 and approximately nineteen-twentieths (19/20) of the circumferential length 110 of the ear compression band 100.

The present ear compression band 100 has several advantages due to the compression band 101 not being completely around the circumferential length 110. If the compression band 101 was completely circumferential, the ear compression band 100 would not be able to accommodate a change in length as described below with respect to the fastening system (see FIGS. 4-6). Further, the compression band 101 not being completely circumferential can increase breathability and/or reduce the bulk of the ear compression band 100 as the compression band 101 can be a thicker, heavier material. The adjustability of the ear compression band 100 prevents the ear compression band 100 and/or the compression band 101 from causing indentations in the head of the user.

The compression band 101 can be coupled with and/or integrally formed with the portion of the circumferential length 110. In at least one instance, the compression band 101 can be stitched, sewn, and/or otherwise coupled with the ear compression band 100 along the portion of the circumferential length 110. In other instances the compression band 101 can be coupled with the ear compression band 100 via adhesive, thermal adhesion, and/or the like. When the compression band 101 is sewn to the ear compression band 100, the coupling of the compression band 101 and the ear compression band 100 can allow for flexing and movement relative to one another while maintaining the desired elastic properties.

The ear compression band 100 can include a material loop 112 operably arranged to receive the compression band 101 therein. The compression band 101 can be coupled with the material loop 112 and/or the ear compression band 100, thereby coupling the compression band 101 with the ear compression band 100. In at least one instance, the compression band 101 can be coupled with the ear compression band 100 along a top longitudinal edge of the compression band 101. The top longitudinal edge of the compression band 101 can be sewn, heat formed, adhesively, and/or otherwise coupled with the ear compression band 100. The top longitudinal edge is the edge of the band that is operable to be installed nearest the crown of the user in one example. In at least one example, only one edge of the band is coupled with the compression band 101 and the other edge is not coupled with the compression band 101. The orientation of the band can be reversible except in the instance of joining with a hat in which the unsewn edge is the lower most edge. This configuration further enhances the comfort of the user as no stitching contacts with the user's ears.

The material loop 112 can be operably formed by rolling up and/or flipping under a portion of the ear compression band 100, thereby forming the material loop 112. The material loop 112 can be operable to provide a portion of the ear compression band 100 and/or substantially similar material between the user's skin and/or head and the compression band 101. This can increase comfort and wearability of the ear compression band 100. In at least one instance, a portion of the ear compression band 100 is rolled up over the compression band 101, thereby allowing the skin surface contacting material to be substantially smooth and/or continuous.

The compression band 101 can be a pliable material that encircles and/or substantially surrounds a user's head from approximately from one temple to the adjacent ear, the back of the head, the opposite ear, and the opposite temple. The ear compression band 100 can fully encircle the user's head. The compression band 101 can be an elastic and/or stretch material disposed having at least a two-way stretch weave. In at least one instance, the compression band 101 can be neoprene. The compression band 101 can be operably arranged to have a stretch direction along the longitudinal length thereof (e.g. along the portion of the circumferential length 110). The elasticity and/or stretch of the compression band 101 can allow the circumferential length 110 to expand and/or retract during placement on a user's head. The ear compression band 100 can similarly have a two-way stretch weave to allow the circumferential length 110 to expand and/or retract with the compression band 101.

The compression band 101 can include, but not limited to, elastic material, braided elastic material, and/or the like. The compression band 101 can be of similar material to elastic waistbands in clothing. These materials can include combinations of rubber and polyester, thereby providing elastic deformation of the material, and thus compression. In at least one instance, the compression band 101 is neoprene.

In some instances, the compression band 101 can include materials including, but not limited to, spandex, cotton, lycra, slinky knits, nylon, rayon, stretch denim, and/or combinations thereof. The ear compression band 100 can be made from other materials. In at least one instance, the ear compression band 100 can be cotton. In other instances, the ear compression band 100 can be a combination of cotton and spandex or bamboo and spandex. In yet other instances, the ear compression band can include materials including, but not limited to, spandex, cotton, lycra, slinky knits, nylon, rayon, stretch denim, and/or combinations thereof.

The compression band 101 can be operable to provide a compression and/or tension on a portion of a user's head. At least a portion of the circumferential length 110 of the ear compression band 100 lacks the compression band 101. The compression band 101 can be operably arranged and/or positioned to pass over one or more of the user's ears and provide a compressive force to pin and/or hold the ear against the user's skull. In at least one instance, the compression band 101 passes over one of the user's ears. In other instances, the compression band 101 passes over both of the user's ears. In yet other instances, the compression band 101 can pass over one of the user's ears while the ear compression band 100 passes over both of the user's ears.

The ear compression band 100 can include a compression band 101 couple therewith and operably arranged to be adjacent to the user's ears when worn. The compression band 101 can be discontinuous such that two distinct compression band 101 elements, one at or adjacent to each ear portion, are coupled with the ear compression band 100. A discontinuous compression band 101 can provide an ear compression band 100 having a rear portion free of the compression band in addition to the front portion 150. In some instances, the discontinuous compression band 101 can be disposed in approximately one-quarter (¼) of the ear compression band 100.

As described above, at least half (½) of the circumferential length 110 has the compression band 101 and no more than nine-tenths (9/10) of the circumferential length 110 has the compression band 101. In some instances, the compression band 101 can be arranged and/or coupled with no more than approximately nineteen-twentieths (19/20) of the circumferential length 110 of the ear compression band 100. In some instances, the compression band 101 can be arranged and/or coupled with between approximately seventeen-twentieths (17/20) of the circumferential length 110 of the ear compression band 100 and approximately nineteen-twentieths (19/20) of the circumferential length 110 of the ear compression band 100.

Figure 2:
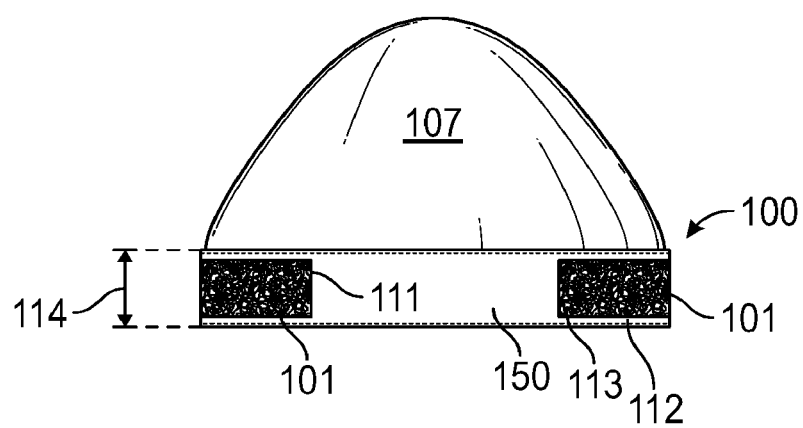
FIG. 2 is an example front sectional view of an ear compression band, according to at least one instance of the present disclosure.

FIG. 2 illustrates a front sectional view of an ear compression band, according to at least one instance of the present disclosure. The ear compression band 100 can include a material loop 112 along at least a portion of the circumferential length 110 (shown in FIG. 1) operable to receive a compression band 101. The material loop 112 can have a predetermined height 114 operable to receive the compression band 101 therein.

As can be appreciated in FIG. 2, the ear compression band 100 can include a hat portion 107. The hat portion 107 can extend from an upper edge of the ear compression band to form a dome-shaped (e.g. spherical dome, spherical cap, etc.), frusto-conincal, conical, and/or any other shape. The hat portion 107 of the ear compression band 100 can be aesthetically pleasing, which can eliminates the obviousness of a medical intervention. The hat portion 107 can be arranged to substantially cover and/or surround a user's head and/or scalp. The hat portion 107 can be made of the same or similar material as the ear compression band 100 and include a two-way or four-way stretch fabric weave to allow comfort and conformity to the user's head.

In some instances, the ear compression band 100 and/or hat portion 107 can have patterns, designs, colors, graphics, and/or other aesthetically pleasing decorative elements. The decorative elements can be unisex and/or gender specific (e.g. bows, glitter, cars, trucks dinosaurs, pink or blue elements).

The hat portion 107 can be detachable from the ear compression band 100. The ear compression band 100 can be implemented with or without the hat portion 107. In at least one instance, one or more hat portions 107 can be interchangeable with the ear compression band 100, thereby allowing stylistic changes to the ear compression band without requiring multiple ear compression bands. Designs, patterns, colors, and/or styles can be adjusted for season, weather, outfit and the like without regarding changing of the ear compression band 100. In other instances, the hat portion 107 is fixed to the ear compression band 100. In yet other instances, the ear compression band 100 and hat portion 107 are integrally made from the same material.

As can further be appreciated in FIG. 2, the compression band 101 can have longitudinally opposed distal end 111, 113, which provides a front portion 150 of the ear compression band 100 without the compression band 101 coupled therewith. In at least one instance, distal end 111 can be operably arranged on a user's left temple while distal end 113 can be operably arranged on user's right temple, thereby positioning the compression band 101 over user's left and right ear, respectively, and around the back of the users head while leaving the user's forehead free of the compression band 101 in the front portion 150.

While the present disclosure is described with respect to the longitudinally opposed distal ends 111, 113 being positioned on a user's temples, it is within the scope of this disclosure that the longitudinally disposed distal ends 111, 113 can be arranged at other positions on the circumferential length. In at least one instance, the longitudinally disposed distal ends 111, 113 can be positioned on a user's ears or immediate adjacent thereto without specific regard to a user's temples. In other instances, the longitudinally distal ends 111, 113 can be positioned between the user's ears and a user's temples (e.g. hair sideburns). The compression band 101 can be operably arranged to pass over the user's ears, thereby providing compression thereto, while not extending across at least a portion of the user's forehead. Therefore, the longitudinally distal ends 111, 113 can be positioned at any location between a user's ear and forehead. Further, the positioning of the longitudinally distal ends 111, 113 does not need to be symmetrical from side-to-side, so long as the compression band 101 passes over both ears while not passing over the forehead.

Figure 3:
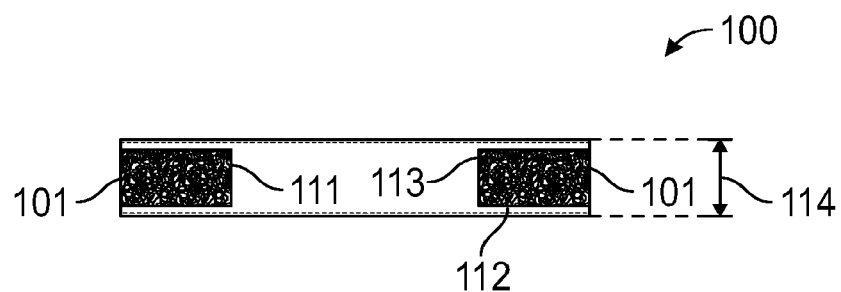
FIG. 3 is an example front sectional view of an ear compression band, according to at least one instance of the present disclosure.

FIG. 3 is an example of a front sectional view of an ear compression band having a compression band operably disposed therein, according to at least one instance of the present disclosure. The ear compression band 100 can include a material loop 112 operably arranged to receive the compression band 101 therein. The compression band 101 can have a front portion 150 void of the compression band 101 and/or the material loop 112. The front portion 150 can be operably arranged to substantially align with a user's forehead during operation, thereby preventing compression on the user's forehead and providing additional comfort. In at least one instance, the front portion 150 can extend between a user's temples across a user's forehead. In other instances, the front portion 150 can be slightly longer or shorter depending on the arrangement of the compression band 101 and/or the distal ends 111, 113 thereof.

As can be appreciated in FIG. 3, the ear compression band 100 can omit the hat portion 107 (shown in FIG. 2) without deviating from the design and/or the present disclosure. The hat portion 107 can be substantially aesthetic and/or of secondary medical value (e.g. shade, warmth, etc.), and thus can be omitted without reducing the efficacy of the ear compression band 100.

Figure 4:
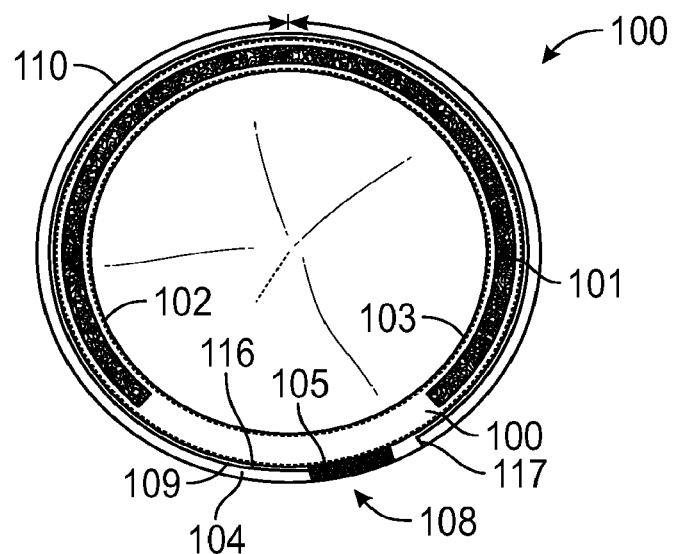
FIG. 4 is a top sectional view of an ear compression band fastener system, according to at least one instance of the present disclosure.

FIG. 4 is a top sectional diagrammatic view of an ear compression band, according to at least one instance of the present disclosure. The ear compression band 100 can include a fastener system 108 to adjust and/or tighten the ear compression band 100 onto a user's head for the appropriate fit. The fastener system 108 can be operably arranged to adjust the ear compression band 100 for an individual user, thus providing a secure fitment and preventing accidental and/or incidental removing of the ear compression band 100 while also preventing the ear compression band 100 and/or the compression band 101 from being too tight and potential indenting the user's head.

The fastener system 108 can be arranged on the front portion 150 of the ear compression band 100. The fastener system 108 can be positioned and/or arranged on the front portion 150 to allow substantially even compression on each of the user's ears (e.g. on both sides of the head). As a newborn and/or infant spends significant amount of time on their back with the back of their head resting against the floor or other surface, the fastening system 108 can be arranged on the front portion to prevent the user's head from resting on the fastening system 108 for extending periods of time.

While the fastener system 108 is operably arranged on the front portion 150, it is within the scope of the present disclosure to implement the fastener system 108 on one side or each side of the ear compression band 100, thereby allowing compression adjust immediately adjacent to a user's ears. A fastener system 108 disposed on one side can allow compression on a single ear while providing little to no compression on the other ear in some instances where only one ear requires compression.

The fastener system 108 can include a first hook/loop portion 104 coupled internally and operable to engage a second corresponding hook/loop portion 105 disposed on the ear compression band. The fastener system 108 can be operable to determine the tightness and fit of the ear compression band 100. The first hook/loop portion 104 and the second corresponding hook/loop portion 105 can be operable to engage with at least a portion of the other respective hook/loop portion, and/or combinations thereof. In at least one instance, the fastening system 108, the first hook/loop portion 104 and/or the second hook/loop portion 105 can be disposed on a portion of the circumferential length 110 void of the compression band 101, thereby providing more flexibility with respect to the fastening system 108, the first hook/loop portion 104, and/or the second hook/loop portion 105.

The first hook/loop portion 104 can be operable to engage with at least a portion of the second corresponding hook/loop portion 105. In other instances, the second corresponding hook/loop portion 105 can be operable to engage with at least a portion of the first hook/loop portion 104. In yet other instances, at least a portion of the first hook/loop portion 104 can be operable to engage with at least a portion of the second corresponding hook/loop portion 105. In at least one instance, the hook and loop fastener system described above with respect to the first hook/loop portion 104 and/or the second corresponding hook/loop portion 105 can be Velcro®. In other instances, the fastening system 108 can be buttons, snaps, magnetic, and/or other adjustable coupling arrangements operable to allow adjustment of the circumferential length 110 of the ear compression band 100.

In at least one instance of the present disclosure, the first hook/loop portion 104 can be a hook portion of the hook and loop fastener and have a first predetermined length and the second hook/loop portion 105 can be a loop portion of the hook and loop fastener and have a second predetermined length. The second predetermined length can be greater than the first predetermined length, thus allowing the first hook/loop portion 104 to operably engage with the second hook/loop portion 105 in a variety of positions while still engaging substantially the entirety of the first predetermined length of the first hook/loop portion 104. The first hook/loop portion 104 and the first predetermined length thereof can be coupled with a proximal end 116 of the second hook/loop portion 105 to maximize the circumferential length 110 of the ear compression band 100. The first hook/loop portion 104 and the first predetermined length thereof can be coupled with a distal end 117 of the second hook/loop portion 105 to minimize the circumferential length 110 of the ear compression band 100.

In some instances, the first hook/loop portion 104 can be a hook portion of the hook and loop fastener and the second hook/loop portion 105 can be a loop portion of the hook and loop fastener, thereby preventing a user from injuring oneself via scratching or abrasion of the hook portion. The first hook/loop portion 104 and the corresponding hook portion can be inward facing such that if a user attempts to scratch, itch, and/or remove the ear compression band 100 only the softer, less abrasive loop portion of the hook/loop fastener would be exposed.

In at least one instance, the first hook/loop portion 104 can be coupled with the ear compression band 100 at a proximal end 109. In at least one instance, the proximal end 109 of the first hook/loop portion 104 can include one or more fabric bunches operable to assist in the adjustment and/or alteration of the circumferential length 110 via the fastening system 108. The one or more fabric bunches can be arranged to allow the first hook/loop portion 104 to extend and therefore couple with the second corresponding hook/loop portion 105, thus shortening the circumferential length 110 of the ear compression band 100.

As the first hook/loop portion 104 is pulled, the one or more fabric bunches can stretch due to the excess material, material weave, and/or elasticity to all the first hook/loop portion 104 to couple with a more distal portion of the second corresponding hook/loop portion. In at least one instance, the second corresponding hook/loop portion 105 can have a predetermined length exceeding the first hook/loop portion 104, thus the first hook/loop portion couples with a portion of the second corresponding hook/loop portion.

When the one or more fabric bunches remain un-stretched the first hook/loop portion 104 can proximally couple with the second corresponding hook/loop portion, whereas when the one or more fabric bunches 115 stretch the first hook/loop portion 104 can couple distally with the second corresponding hook/loop portion 105.

The one or more bunches 115 and/or a portion of the fastening system 108 can be affixed to the ear compression band 100 and/or another portion of the fastening system 108 can be coupled to the ear compression band 100 through a tab joined to the ear compression band 100 at the portion of the ear compression band 100 at which the compression band 101 is not coupled therewith. The tab can be operably arranged to compress a portion that is double stitched to the ear compression band and create a fold thereon. In at least one instance, the tab can be coupled with the ear compression band 100 and structured to fold and/or pivot at the coupling point between the ear compression band 100 and the tab, thereby allowing the circumferential length 110 adjustable.

Figure 5:
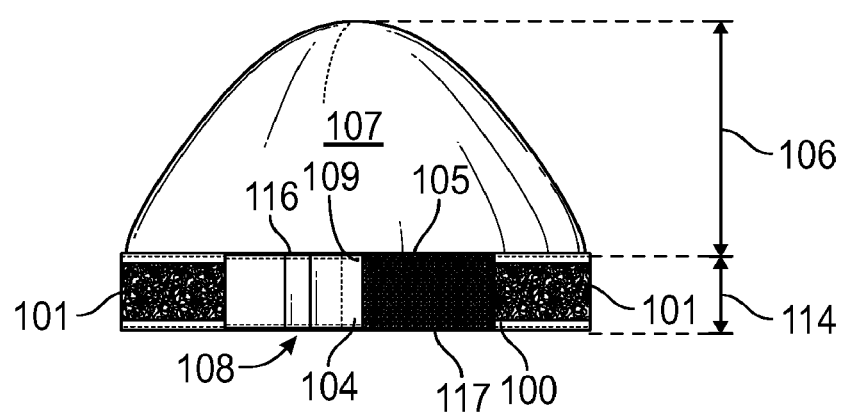
FIG. 5 is a frontal sectional view of a fastener on an ear compression band, according to at least one instance of the present disclosure.

FIG. 5 illustrates the front diagrammatic sectional view of an ear compression band including a fastener system. The fastener system 108 on a hat rim of the ear compression band 100 and/or the compression band 101. Depending on the age, head size, and/or ear size of the child, the dimensions can shift, change, and/or be adjusted. The compression band 101 can have a circumferential length between approximately 10" and approximately 20" and a width between approximately 1" and approximately 3". The ear compression band 100 can have a circumferential length between approximately 13" and approximately 24" and in height between approximately 1.2" and approximately 3.2". The ear compression band 100 can have a circumferential length between approximately 13" and approximately 16" and in height between approximately 1" and approximately 2". The first hook/loop portion 104 of the ear compression band 100 can have a length between approximately 1" and approximately 4" and a width of the first hook/loop portion 104 can be substantially the same size as the width of the compression band. In at least one instance, a width of the first hook/loop portion 104 can be approximately 1.5". The second corresponding hook/loop portion 105 can extend along at least a portion of the circumferential length between approximately 2" and approximately 6" and a width of the second hook/loop portion 105 can be substantially the same size as the width of the compression band. In at least one instance, a width of the second hook/loop portion 105 can be approximately 1.5". In some instances in which the ear compression band 100 includes a hat portion 107, the hat portion 107 can have a height 106 between approximately 4" and approximately 12".

Figure 6:
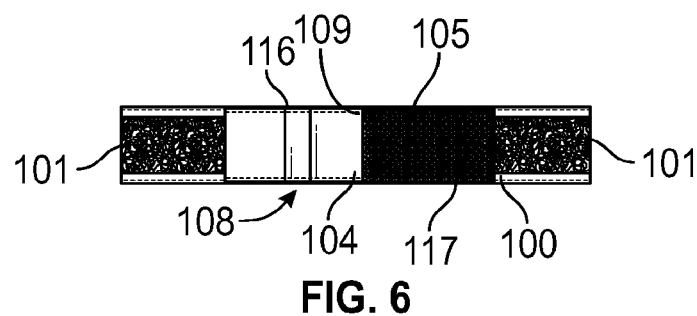
FIG. 6 is an example frontal sectional view of the fastener on a material loop and the compression band, according to at least one instance of the present disclosure.

FIG. 6 is an example of the frontal sectional view of the fastener on an ear compression band and/or a compression band. As discussed above with respect to FIG. 5, the dimensional arrangements of the ear compression band 100 and/or the compression band 101 can be substantially the same with and/or without the hat portion 107.

Figure 7A:
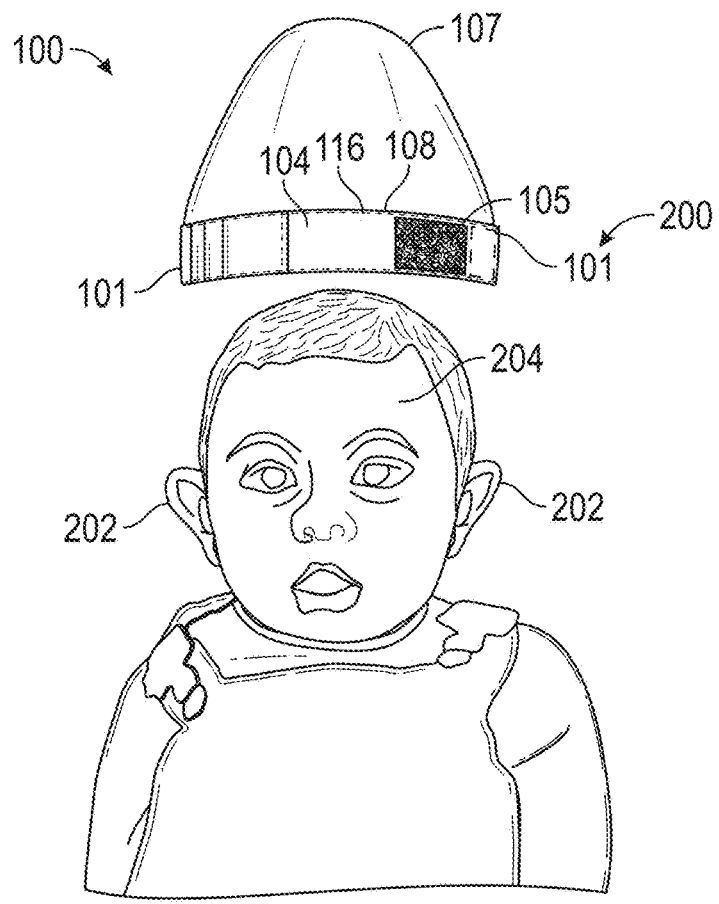
FIG. 7A is an isometric view of an ear compression band arranged to be disposed around a user's head, according to at least one instance of the present disclosure.

FIG. 7A is an illustrative view of an ear compression band prior to positioning on a user. The ear compression band 100 can be operable to assist as a non-invasive, non-medical ear deformity correction in infants and/or toddlers by positioning the ear against the head and allowing the corresponding tissue to develop (e.g. harden) appropriately. The ear compression band 100 can be positioned around a user's (e.g. newborn or infant) head 200 with a compression band 101 positioned on the rear side of the head 200.

The compression band 100 is positioned to extend over at least each ear 202 of the user, thereby being operable to compress and/or position the ear 202 against the user's head. In some instances, the compression band 101 can extend to a user's temples across the ear 202 around the rear of the head 200 to the opposing ear. As can be appreciated in FIG. 7A, while the compression band 101 is arranged to extend only over a rear portion of the user's head 200 and across the ears 202, the ear compression band 100 is operable to extend around the entirety of the user's head 200 including across the forehead 204. A front portion 150 of the ear compression band 100 is arranged across the user's forehead 204, the front portion 150 not having the compression band 101 coupled therewith.

Figure 7B:
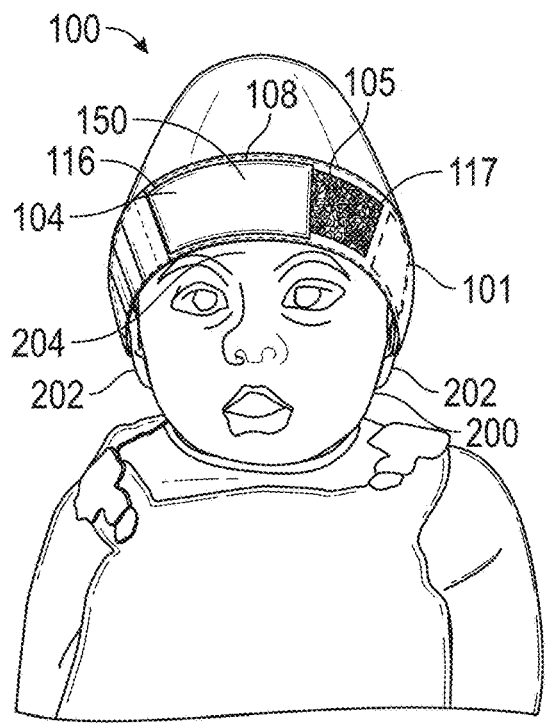
FIG. 7B is an isometric view of an ear compression band disposed around a user's head, according to at least one instance of the present disclosure.

FIG. 7B is an illustrative view of an ear compression band positioned and engaged on a user. The ear compression band 100 can be positioned and/or arranged over the user's ear 202, thereby compressing the user's ear 202 against the user's head 200. The ear compression band 100 can include a front portion 150 operably positioned across the user's forehead 204. The front portion 150 can include a fastening system 108 operable to adjust the circumferential length of the ear compression band 100 for a personalized fit to the user's head 200. The fastening system 108 can include a first hook/loop portion 104 and a second corresponding hook/loop portion 105 operable to engage, respectively, at an operator defined length. The operator (e.g. parent, caregiver, babysitter, etc.) can adjust the circumferential length 110 of the ear compression band 100 via engagement between the first hook/loop portion 104 and the second corresponding hook/loop portion 105. The operator can adjust the circumferential length 110 to ensure the ear compression band 100 appropriately compressions the ear 202 against the user's head 200. The fastening system 108 can be utilized to increase and/or decrease the circumferential length 110 of the ear compression band 100, thereby ensuring a comfort fit and preventing accidental and/or incidental removal of the ear compression band 100.

The ear compression band 100 can be arranged on the user's head 200 and have the fastening system 108 adjusted for proper securement relative to the size of the user's head 200. The first hook/loop portion 104 can be arranged to cover at least a portion of the second hook/loop portion 105. As can be appreciated in FIG. 7B, the first hook/loop portion 104 does not reach the distal end 117 of the second hook/loop portion 105, thereby allowing the ear compression band 100 to be adjusted smaller should the circumferential length 110 be too large relative to the user's head 200. In instances where the circumferential length 110 is not large enough for the user's head 200, the first hook/loop portion 104 can be adjusted toward the proximal end 116 of the second hook/loop portion 105.

Figure 7C:
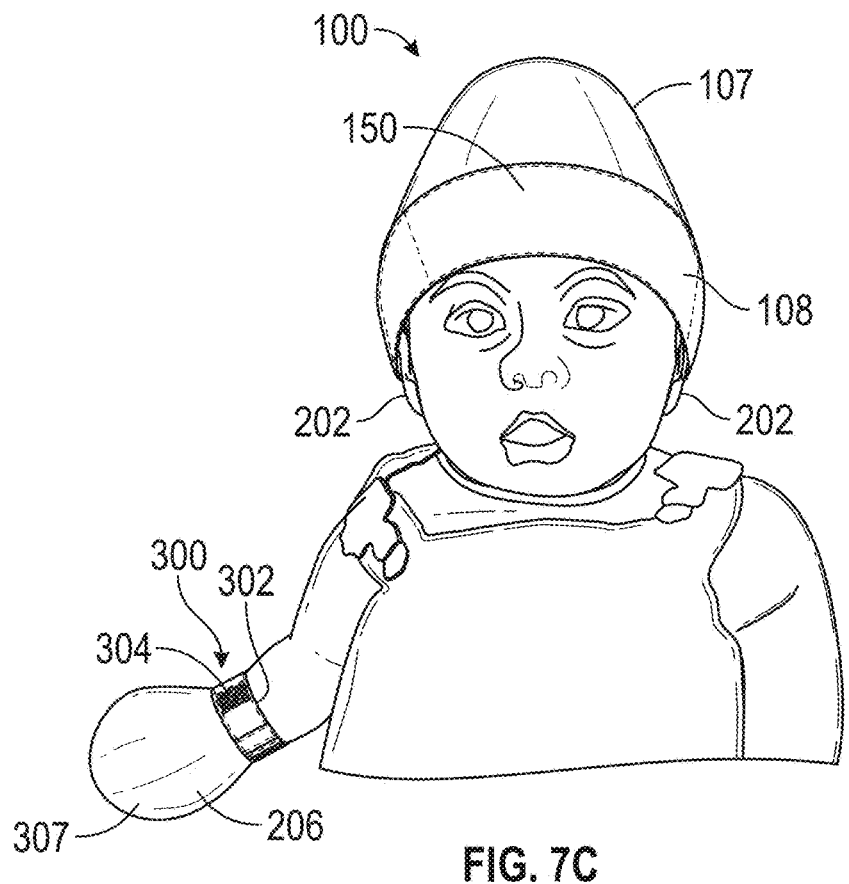
FIG. 7C is an isometric view of an ear compression band engaged on a user having the fastening system tightened and a mitten engaged on a user having the fastening system tightened, according to at least one instance of the present disclosure.

FIG. 7C is an illustrative view of an ear compression band positioned and engaged on a user having the fastening system tightened. As can be appreciated in FIG. 7C, the first hook/loop portion 104 can extend to the distal end 117 of the second hook/loop portion 105, thereby substantially covering the second hook/loop portion 105 and reducing the circumferential length 110. The ear compression band 100 can have the circumferential length 110 adjust to fit user's with different size heads and/or to allow adjustment as the user grows and their head size changes during development.

The ear compression band 100 as described herein can further be implemented in other instances. For example, the teaching presented herein can be operable with mittens 300 disposed on one or more of the user's hands 206. The mittens can be implemented to assist in preventing the accidental and/or incidental removal of the compression band during use. Additionally, the mittens 300 can protect the user 200 from accidental and/or incidental scratching from the user's fingernails. The mittens 300 can have an opening 302 formed at one end thereof and operable to receiver a user's hand 206 therein including four fingers and a thumb. The mitten 300 can extend partially down a user's arm to aid in attachment and/or prevent user 200 removal. In at least one instance, the mittens 300 can extend over a user's wrist.

The mittens 300 can include a fastening system 304 using a hook and loop fastener arrangement to allow proper securement of the mittens 300 with the user's hands 206 to prevent removal thereof. The fastening system 304 can include a first hook/loop portion and a second hook/loop portion, thereby allowing adjustment of the opening 302. The first hook/loop portion can be operable to engage with and/or couple with at least a portion of the second hook/loop portion. Care must be taken not to over tight the fastening system 304, which would reduce blood circulation to the user's hands 206, but also tightening the fastening system 304 sufficient to prevent user removal of the mittens 300.

The mittens 300 of the present disclosure can be implement with the compression band 100 disclosed herein and/or independent of the compression band 100. The mittens 300 can be implemented to prevent accidental and/or incidental scratching by the newborn and/or infant user 200. In at least one instance of the present disclosure, the first hook/loop portion 309 can be a hook portion of the hook and loop fastener and have a first predetermined length and the second hook/loop portion 305 can be a loop portion of the hook and loop fastener and have a second predetermined length. The second predetermined length can be greater than the first predetermined length, thus allowing the first hook/loop portion 309 to operably engage with the second hook/loop portion 305 in a variety of positions while still engaging substantially the entirety of the first predetermined length of the first hook/loop portion 309. The first hook/loop portion 309 and the first predetermined length thereof can be coupled with a proximal end 316 of the second hook/loop portion 305 to maximize the circumferential length 310 (see FIG. 7E) of the ear compression band 300. The first hook/loop portion 309 and the first predetermined length thereof can be coupled with a distal end 317 of the second hook/loop portion 305 to minimize the circumferential length 310 of the ear compression band 300.

Figure 7D:
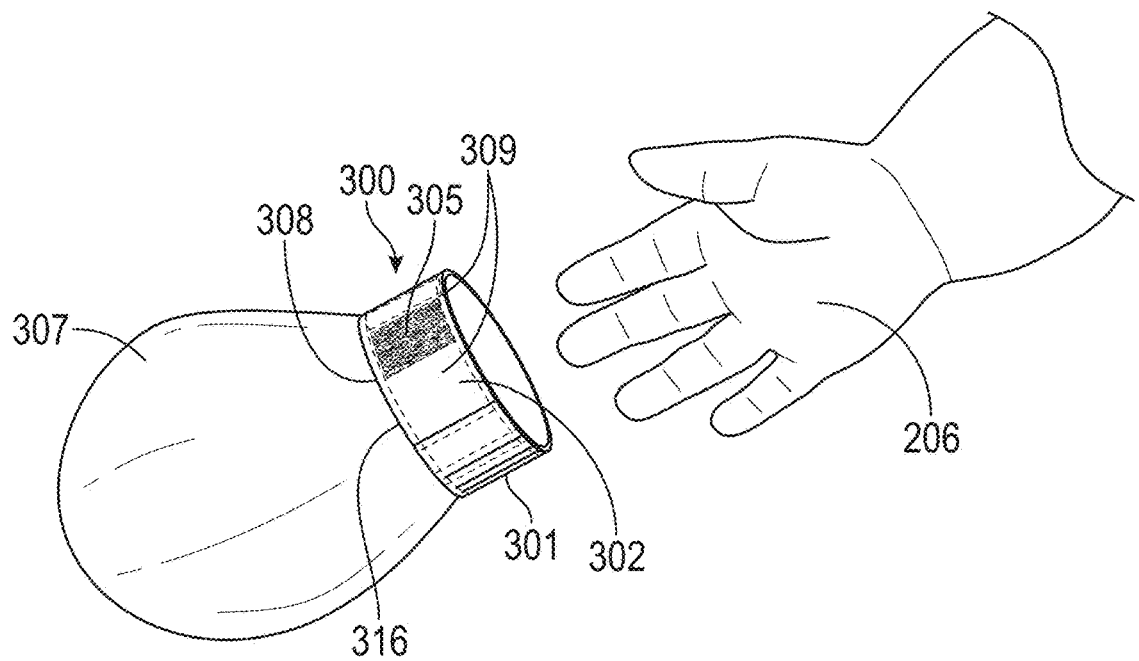
FIG. 7D is an isometric view of an ear compression band engaged on a user having the fastening system tightened and a mitten for a user, according to at least one instance of the present disclosure.

FIG. 7D illustrates a mitten 307 being removed from a user's hand 206. The mitten can have an opening formed to receive a user's hand 206. The opening has a circumferential length and the mitten 307 can contain the four fingers and thumb together in a single article.

FIG. 7E illustrates the top sectional view of a mitten 307 with a continuous compression band, according to at least one instance of the present disclosure. A mitten 307 can have continuous compression band 300, which includes a compression band 301 operable coupled with at least a portion thereof. The continuous compression band 300 can include a fastener system 308 to adjust and/or tighten the continuous compression band 100 onto a user's hand for the appropriate fit. The continuous compression band 300 can include a material loop 312 operably arranged to receive the compression band 301 therein. The compression band 301 can be coupled with the material loop 312 and/or the continuous compression band 300, thereby coupling the compression band 301 with the continuous compression band 300. The compression band 301 can be substantially circular, and the compression band 301 can be coupled with at least one-half (1/2) of a circumferential length 310 of the continuous compression band 300. In some instances, the compression band 301 can be arranged and/or coupled with no more than approximately nineteen-twentieths (19/20) of the circumferential length 310 of the continuous compression band 300. In some instances, the compression band 301 can be arranged and/or coupled with between approximately seventeen-twentieths (17/20) of the circumferential length 310 of the ear compression band 300 and approximately nineteen-twentieths (19/20) of the circumferential length 310 of the continuous compression band 300. As can further be appreciated in FIG. 7E, the compression band 301 can have longitudinally opposed distal end 311, 313, which provides a front portion 350 of the continuous compression band 300 without the compression band 301 coupled therewith.

FIG. 8 illustrates a flowchart for an example method of use for an ear compression band. The method 800 can be implemented with regard to FIGS. 1-7C as described above, and can include one or more blocks. Method 800 can include more or less blocks than those detailed below, and the arrangement of blocks can be adjusted without deviating from method 800 and/or the present disclosure. The method 800 can begin at block 802.

At block 802, a user can receive an ear compression band having a substantially circular shape and the ear compression band having a circumferential length. In at least one instance, the user can be a newborn and/or infant child. The ear compression band can have a compression band operably coupled with at least one-half (1/2) of the circumferential length. The ear compression band can have a length and configuration as described above. The method 800 can proceed to block 804.

At block 804, the ear compression band can be positioned on a user's head with the compression band disposed on a rear portion of a user's head. The compression band can have longitudinally distal ends with a first distal end is arranged at one user's ear and a second distal end arranged at the user's opposing ear. The method 800 can proceed to block 806.

At block 806, a fastening system coupled with the ear compression band can be adjusted, thereby reducing and/or increasing the circumferential length of ear band based on the user's head size.

While the present disclosure has provided representative measurements for use on a newborn and/or infant child for ear compression, it is within the scope of this disclosure to adjust, alter, vary, and/or increase/decrease the dimensions depending on the user and/or the user's exact measurements. Additionally, the representative measurements can be increased and/or decreased for users of an older and/or younger nature.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in matters of shape, size and arrangement of the parts within the principles of the present disclosure up to, and including, the full extent established by the broad general meaning of the terms used in the claims.

Statement Bank of the Claims

STATEMENT 1: An ear compression apparatus comprising an ear compression band having a substantially circular shape, the ear compression band having a circumferential length; and a compression band spans and is operably coupled with at least one-half (1/2) of the circumferential length, wherein the compression band spans and is coupled with less than nineteen-twentieths (19/20) of the circumferential length of the ear compression band, thereby forming a front portion of the circumferential length not having a compression band coupled therewith.

STATEMENT 2: The ear compression apparatus of Statement 1, wherein the compression band spans and is coupled with at least seventeen-twentieths (17/20) of the circumferential length of the ear compression band.

STATEMENT 3: The ear compression apparatus of Statement 1 or Statement 2, further comprising a fastening system operable to adjust the circumferential length of the ear compression band, wherein a portion of the fastening system is affixed to the ear compression band and another portion of the fastening system is coupled to the ear compression band through a tab joined to the ear compression band at the portion of the ear compression band at which the compression band is not coupled therewith.

STATEMENT 4: The ear compression apparatus of any one of Statements 1-3, wherein the tab compresses a portion that is double stitched to the ear compression band and creates a fold thereon.

STATEMENT 5: The ear compression apparatus of any one of Statements 1-4, wherein the ear compression band includes a material loop operable to receive at least a portion of the compression band therein.

STATEMENT 6: The ear compression apparatus of any one of Statements 1-5, wherein a hat portion extends from an upper edge of the ear compression band.

STATEMENT 7: The ear compression apparatus of any one of Statements 1-6, wherein the hat portion is spherical dome shaped.

STATEMENT 8: The ear compression apparatus of any one of Statements 1-7, wherein the hat portion is substantially frusto-conical.

STATEMENT 9: The ear compression apparatus of any one of Statements 1-8, wherein the compression band has a width between approximately 1 inch and approximately 2 inches.

STATEMENT 10: The ear compression apparatus of any one of Statements 1-9, wherein the ear compression band has a width between approximately 1 inches and approximately 4 inches.

STATEMENT 11: The ear compression apparatus of any one of Statements 1-10, further comprising a hook and loop fastening system operable to adjust the circumferential length of the ear compression band.

STATEMENT 12: The ear compression of any one of Statements 1-11, wherein fastening system includes a first hook portion and a second loop portion, wherein at least a portion of the first hook portion is operable to engage with at least a portion of the second loop portion.

STATEMENT 13: An ear compression system comprising an ear compression band having a substantially circular shape, the ear compression band having a circumferential length operable to be arranged around a user's head, a compression band operably coupled with at least one-half (½) of the circumferential length, the compression band operably to be positioned on the user's head spanning from approximately from at least one ear around a rear of the user's head to an opposing ear, wherein the compression band is coupled with less than nine-tenths (9/10) of the circumferential length of the ear compression band; and a front portion formed along the circumferential length not having a compression band coupled therewith, the front portion operable to be positioned along a user's forehead.

STATEMENT 14: The ear compression apparatus of Statement 13, wherein the ear compression band includes a material loop operable to receive at least a portion of the compression band therein.

STATEMENT 15: The ear compression apparatus of Statement 13 or Statement 14, wherein a hat portion extends from an upper edge of the ear compression band.

STATEMENT 16: The ear compression apparatus of any one of Statements 13-15, wherein the hat portion is spherical dome shaped.

STATEMENT 17: The ear compression apparatus of any one of Statements 13-16, wherein the hat portion is substantially frusto-conical.

STATEMENT 18: The ear compression apparatus of any one of Statements 13-17, wherein the compression band has a width between approximately 1 inch and approximately 2 inches.

STATEMENT 19: The ear compression apparatus of any one of Statements 13-18, wherein the ear compression band has a width between approximately 1 inches and approximately 4 inches.

STATEMENT 20: A method of use for an ear compression band, comprising receiving an ear compression band having a substantially circular shape and the ear compression band having a circumferential length, the ear compression band having a compression band operably coupled with at least one-half (½) of the circumferential length; positioning the ear compression band on a user's head with the compression band disposed on a rear portion of a user's head, wherein the compression band has longitudinally distal ends with a first distal end is arranged at one user's ear and a second distal end arranged at the user's opposing ear; adjusting a fastening system coupled with the ear compression band, thereby reducing and/or increasing the circumferential length of ear band based on the user's head size, wherein the compression band is coupled with less than nine-tenths (9/10) of the circumferential length of the ear compression band, thereby forming a front portion of the circumferential length not having a compression band coupled therewith.

STATEMENT 21: The method of Statement 20, wherein the ear compression band includes a material loop operable to receive at least a portion of the compression band therein.

STATEMENT 22: The method of Statement 20 or 21, wherein a hat portion extends from an upper edge of the ear compression band.

STATEMENT 23: The method of any one of Statements 20-22, wherein fastening system includes a first hook/loop portion and a second hook/loop portion, wherein at least a portion of the first hook/loop portion is operable to engage with at least a portion of the second hook/loop portion.

What is claimed is:

1. A mitten for covering a hand of a newborn and/or an infant user comprising:
    an opening formed at one end of the mitten, the opening operable to receive a user's hand, the opening having a circumferential length, wherein the mitten contains the four fingers and thumb together in a single article;
    a continuous compression band configured to substantially encircle, when worn, a wrist of the user, forming a front portion of the circumferential length not having the compression band coupled therewith;
    a material loop operable to receive a portion of the compression band therein; and
    wherein the compression band spans and is coupled with at least one-half (½) and less than nineteen-twentieths (19/20) of the circumferential length.

2. The mitten of claim 1, further comprising a fastening system operable to adjust the circumferential length, wherein a portion of the fastening system is affixed to mitten and another portion of the fastening system is coupled to the mitten through a tab joined to the mitten at which the compression band is not coupled therewith.

3. The mitten of claim 2, wherein the tab includes a portion that is double stitched and compresses the mitten and creates a fold thereon.

* * * * *